(12) United States Patent
Seaver (10) Patent No.: US 9,668,663 B2
(45) Date of Patent: Jun. 6, 2017

(54) IMPLANTABLE DUAL SENSOR BIO-PRESSURE TRANSPONDER AND METHOD OF CALIBRATION

(71) Applicant: Arkis Biosciences, Knoxville, TN (US)

(72) Inventor: Chad Eric Seaver, Knoxville, TN (US)

(73) Assignee: Arkis Biosciences, Knoxville, TN (US)

( * ) Notice: Subject to any disclaimer, the term of this patent is extended or adjusted under 35 U.S.C. 154(b) by 8 days.

(21) Appl. No.: 14/667,377

(22) Filed: Mar. 24, 2015

(65) Prior Publication Data

US 2015/0265171 A1 Sep. 24, 2015

Related U.S. Application Data

(60) Provisional application No. 61/969,789, filed on Mar. 24, 2014.

(51) Int. Cl.
*A61B 5/00* (2006.01)
*A61B 5/03* (2006.01)

(52) U.S. Cl.
CPC ............ *A61B 5/031* (2013.01); *A61B 5/0002* (2013.01); *A61B 5/0031* (2013.01); *A61B 5/032* (2013.01); *A61B 5/6852* (2013.01); *A61B 5/6868* (2013.01); *A61B 2560/0219* (2013.01); *A61B 2560/0228* (2013.01); *A61B 2560/0257* (2013.01); *A61B 2562/0214* (2013.01); *A61B 2562/0233* (2013.01)

(58) Field of Classification Search
CPC ..... A61B 5/031; A61B 5/0002; A61B 5/6852; A61B 5/032; A61B 2560/0257
USPC ......................................................... 600/561
See application file for complete search history.

(56) References Cited

U.S. PATENT DOCUMENTS

| 3,943,915 A | 3/1976 | Severson |
| 4,062,354 A | 12/1977 | Taylor et al. |
| 4,127,110 A | 11/1978 | Bullara |
| 4,471,786 A | 9/1984 | Inagaki et al. |
| 4,660,568 A | 4/1987 | Cosman |

(Continued)

FOREIGN PATENT DOCUMENTS

| EP | 0018207 B1 | 3/1984 |
| EP | 0447545 B1 | 3/1994 |

(Continued)

OTHER PUBLICATIONS

International Search Report and Written Opinion issued in International Application No. PCT/US2015/022284 mailed Jun. 29, 2015.

(Continued)

*Primary Examiner* — Max Hindenburg
*Assistant Examiner* — Jonathan M Foreman
(74) *Attorney, Agent, or Firm* — Meunier Carlin & Curfman LLC (57) ABSTRACT

A bio-pressure sensor system is disclosed, comprising a first sensor configured to provide a reference pressure measurement and second sensor configured to measure a fluid pressure within a human body. The bio-pressure sensor system also comprises a first reference element and second reference element. The first and second sensors share the first reference element. The second reference element is coupled to the first sensor and configured to provide a reference pressure. The first and second sensors each comprise independent output signals.

14 Claims, 6 Drawing Sheets

(56) References Cited

U.S. PATENT DOCUMENTS

| | | |
|---|---|---|
| 4,738,267 A | 4/1988 | Lazorthes et al. |
| 4,787,396 A | 11/1988 | Pidorenko |
| 5,400,794 A * | 3/1995 | Gorman ............... A61B 5/222 128/903 |
| 5,437,284 A | 8/1995 | Trimble |
| 6,113,553 A | 9/2000 | Chubbuck |
| 6,248,080 B1 | 6/2001 | Miesel et al. |
| 6,481,292 B1 * | 11/2002 | Reich ............... A61B 5/0215 73/730 |
| 6,533,733 B1 * | 3/2003 | Ericson ............ A61B 5/0031 128/903 |
| 7,413,547 B1 | 8/2008 | Lichtscheidl et al. |
| 7,785,268 B2 | 8/2010 | Miethke et al. |
| 8,622,923 B2 | 1/2014 | Pons et al. |
| 2004/0106874 A1 | 6/2004 | Eigler et al. |
| 2004/0186367 A1 | 9/2004 | Fresco |
| 2009/0216149 A1 | 8/2009 | Neff et al. |
| 2010/0218612 A1 * | 9/2010 | Ohtani ............... G01L 13/025 73/716 |
| 2011/0066072 A1 | 3/2011 | Kawoos et al. |
| 2011/0160560 A1 | 6/2011 | Stone |
| 2012/0041510 A1 | 2/2012 | Gerbet et al. |
| 2012/0265028 A1 | 10/2012 | Hughes et al. |
| 2013/0018277 A1 | 1/2013 | Liu |
| 2013/0247644 A1 | 9/2013 | Swoboda et al. |
| 2013/0289422 A1 | 10/2013 | Swoboda et al. |
| 2014/0135647 A1 | 5/2014 | Wolf, II |
| 2014/0298884 A1 * | 10/2014 | Mindlin ............ G01L 9/0047 73/1.63 |

FOREIGN PATENT DOCUMENTS

| | | |
|---|---|---|
| EP | 0888744 B1 | 10/2002 |
| EP | 2464279 A1 | 6/2012 |
| EP | 2675343 A2 | 12/2013 |
| WO | 9105575 | 5/1991 |
| WO | 9732519 | 9/1997 |
| WO | 0203859 A1 | 1/2002 |
| WO | 2011018706 A1 | 2/2011 |
| WO | 2012112819 A2 | 8/2012 |
| WO | 2014076620 A1 | 5/2014 |

OTHER PUBLICATIONS

International Preliminary Report on Patentability in International Application No. PCT/US2015/022284, mailed Oct. 6, 2016.

* cited by examiner

Fig. 5

IMPLANTABLE DUAL SENSOR BIO-PRESSURE TRANSPONDER AND METHOD OF CALIBRATION

CROSS REFERENCE TO RELATED APPLICATION

This application claims priority to U.S. Provisional Patent Application No. 61/969,789, filed Mar. 24, 2014, and incorporated herein in its entirety.

FIELD OF INVENTION

The present general inventive concept relates to systems and methods of accurately assessing bodily fluid pressures, such as cerebral spinal fluid (CSF), and more particularly, to multiple pressure sensors within a transponder, and the calibration, processing, and presentation methods of carrying out the same.

BACKGROUND

The human body is comprised of various organs that generate, or are subject to, a variety of pressures. These pressures are primarily induced externally due to gravity and include atmospheric compression and body weight opposition. However, there are also a wide range of pressures produced within the body itself. These pressures include those generated by the cardiovascular system, urinary system, digestive tract, musculoskeletal system, central nervous system, osmotic cell pressures, among others. Most of these pressures are critical for proper health and must be precisely regulated. Blood pressure of the cardiovascular system and cerebral spinal fluid (CSF) of the central nervous system are two such components that must be precisely maintained. The ability to continuously monitor these pressures would allow for early detection and intervention in the event autoregulation becomes impaired.

Intracranial pressure is among the most critical found within the body whereby intracranial hypotension, resulting in brain matter migration, can lead to ruptured blood vessels along the surface of the brain and hematomas while CSF hypertension can lead to decreased blood perfusion within the brain. Either case can quickly become life-threatening and is estimated to affect one to two percent of the population congenitally by hydrocephalus, or acquired due to brain tumor, traumatic obstruction, or damage to the arachnoid villi from meningitis, for example.

Long term monitoring of intracranial pressures (ICP) induced by CSF is of particular interest since chronic elevated ICP is common in patients with hydrocephalus and can become life-threatening in acute cases or when shunt treatments fail or if left untreated. However, current state of the art monitoring devices require sensors to be placed within the brain and tethered to bedside equipment in order to measure the pressure. Such measurements typically only allow ICP monitoring for days at a time, due to both the required invasiveness and also due to sensor drift, and require an acute care clinic setting to facilitate these complicated and risky measurements. Patient position becomes critical for accurate measurements by these systems and since the sensor is percutaneously tethered from within the brain to a bedside instrument, the risk of infection is high. What is needed is a self-contained long-term implantable bio-pressure sensor transponder to facilitate recurring and extended in-vivo CSF pressure measurement assessments non-invasively, ex-vivo, and which can be routinely calibrated for accurate long-term assessment thereby overcoming sensor drift errors and limitations.

SUMMARY

A bio-pressure sensor system is disclosed, comprising a first sensor configured to provide a reference pressure measurement and second sensor configured to measure a fluid pressure within a human body. The bio-pressure sensor system also comprises a first reference element and second reference element. The first and second sensors share the first reference element. The second reference element is coupled to the first sensor and configured to provide a reference pressure. The first and second sensors each comprise independent output signals.

A method for calibration of a bio-pressure sensor implanted in a patient is also disclosed herein. The method comprises measuring a first pressure, via a first pressure sensor, with the patient in a first position, and measuring a second pressure, via the first pressure sensor, with the patient in a second position. The method also includes providing a first reference pressure and a second reference pressure, and calculating a gain correction, m, based on the first pressure, second pressure, first reference pressure, and second reference pressure.

An additional method for calibration of a bio-pressure sensor implanted in a patient is disclosed herein. The method comprises measuring a first pressure, via a first pressure sensor, measuring a first environmental pressure coincident with the first pressure; measuring a second pressure, via the first pressure sensor; measuring a second environmental pressure coincident with the second pressure; and calculating a gain correction, m, based on the first pressure, second pressure, first environmental pressure, and second environmental pressure.

Additional systems and methods are described herein.

BRIEF DESCRIPTION OF THE DRAWINGS

The following embodiments are representative of example techniques and structures designed to carry out various objectives of the present general inventive concept, but those skilled in the art will appreciate that the present general inventive concept is not limited to these example embodiments, and that other techniques and structures could be chosen with sound engineering judgment to achieve the same or similar results as the example embodiments described herein. Moreover, in the accompanying drawings and illustrations, the sizes and relative sizes, shapes, and qualities of lines, entities, and regions may be exaggerated for clarity. A wide variety of additional embodiments will be more readily understood and appreciated through the following detailed description of the exemplary embodiments, with reference to the accompanying drawings in which:

FIG. 4 is a schematic of an example embodiment of the bio-pressure sensor apparatus showing a block diagram for electronic signal conditioning and transcutaneous non-invasive assessment, or the like.

FIG. 5 is a schematic of an additional example embodiment of the bio-pressure sensor apparatus also showing a block diagram for electronic signal conditioning and transcutaneous non-invasive assessment, or the like.

DETAILED DESCRIPTION

Reference will now be made to example embodiments of the present general inventive concept, examples of which are illustrated in the accompanying drawings and illustrations. The example embodiments are described herein in order to explain the present general inventive concept by referring to the figures.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Example embodiments of the present general inventive concept can be utilized to realize a recurring non-invasive, real time, in-vivo pressure measurement transponder, which can be calibrated and interrogated ex-vivo, such as that which would be used to assess CSF pressures in a hydrocephalus patient.

An implantable pressure sensor system and method of calibration is provided for the measurement of fluid pressures within the human body. In one embodiment, the system comprises in-vivo dual pressure sensors, whereby one sensor provides a position dependent transfer function as a reference signal, the other sensor sensing the desired bodily fluid pressure, an amplifier, encoding circuitry, and telemetry unit allowing electromagnetic transcutaneous powering, calibration, and interrogation of the sensor system through the use of an ex-vivo telemetric processing module(s) which calibrates the implanted pressure sensors against known pressure references and then accurately assesses and presents the desired bodily fluid pressure to a user.

The sensors may be of the piezo-resistive, capacitive, optical interferometric type, or other pressure to electrical transduction means, so as to ultimately provide an electronic signal proportional to pressure. Such pressure signals may then be encoded into a transmission signal whereby the signal may be modulated by amplitude, frequency, phase, or temporally such as in the case of pulse width modulation (PWM), in order to encode information proportional to the measured pressure signal. One such method to encode the pressure sensor signal is to compare an electrical pressure sensor output to a predetermined ramp signal, whereby a start to finish signal marker can provide a temporally encoded signal that is essentially a pulse width modulated signal. Alternatively, a particular frequency response may be utilized as a signature proportional to pressure whereby an element of the sensor may be combined with an oscillator to facilitate a shift in resonance or damping to encode pressure into a carrier signal. In the case of a damping modulation, temporal encoding is provided and a receiving circuit would measure the exponential or otherwise decay (e.g. PWM) as representative of a proportional pressure.

Precise pressure measurement may be provided by a differential pressure sensor with a first absolute pressure reference and by offering substantially identical or similar dual pressure sensors, providing individual output signals for each, whereby a subcutaneous second reference fluid column may be utilized by a first sensor, which presents a second reference pressure as a function of position, or other ex-vivo controllable means or methods, to produce a known offset for calibration, and a second pressure sensor for the determination and measurement of a desired in-vivo fluid pressure. Optionally, a means of switching between the second reference pressure to the second sensor and the bodily fluid to the first sensor and vice versa may be incorporated so as each fluid can selectively stimulate the opposite sensor. Furthermore, the second reference pressure may optionally be implemented by means of an electromagnetic actuator, providing a predetermined pressure by means of a piston, solenoid, or any other volume change mechanism, which can be remotely actuated ex-vivo, for example.

The powering of the long-term implantable bio-pressure transponder containing the sensors may be provided by means of telemetry whereby an inductive or optical link can transfer signals of such magnitude as to power or charge the implanted electronic circuitry from an external powering device and also to deliver or receive data. In a similar means, an inductive, optical, or other electromagnetic method may be utilized to send signals proportional-to or encoded-by the measured in-vivo pressures to a receiver external to the patient to accomplish non-invasive transcutaneous assessment. Optionally, such powering and signal transfer may use the same transcutaneous method and frequency over a means such as inductive, radio frequency, optical, or other transfer means.

Figure 1A:
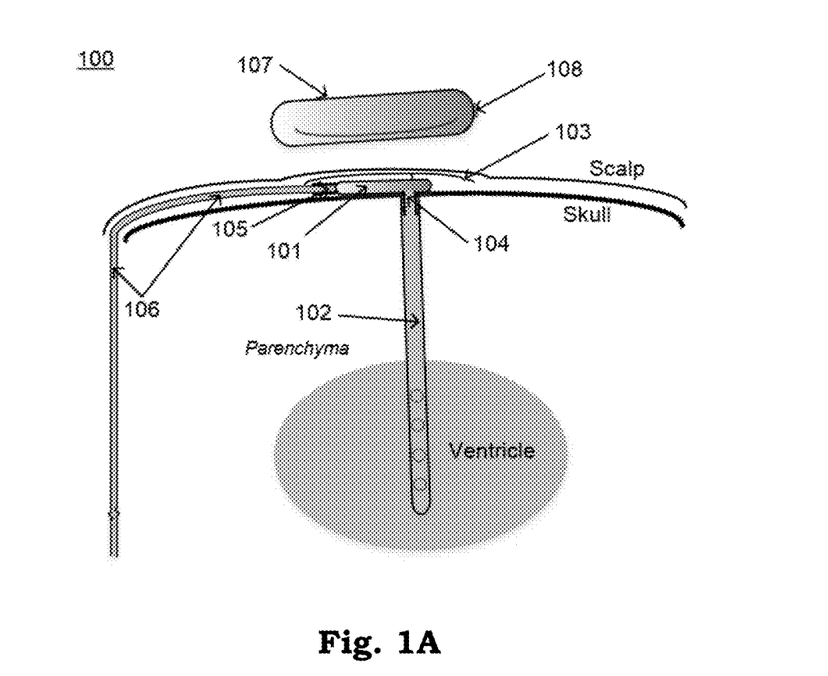
FIG. 1A is a schematic of an example embodiment of the bio-pressure sensor system showing subcutaneous implantation of the bio-pressure sensor unit, or transponder, with a ventricular catheter and reference fluid column.

FIG. 1A is an example embodiment of the bio-pressure sensor system showing subcutaneous implantation of the bio-pressure sensor unit, or transponder, containing multiple sensors, with a ventricular catheter and reference fluid column for long term assessment of CSF pressure along with an ex-vivo telemetric processing unit.

A schematic representation of a subcutaneous bio-pressure sensor system is generally indicated by 100. The bio-pressure sensor transponder is located subcutaneous and is contained within bio-compatible housing 101 with ICP inlet port 104, which can optionally be connected to catheter 102 extending into the brain's ventricle. Housing 101 may be constructed from, but is not limited to, such biocompatible materials as titanium, platinum, ceramic, or glass and may be hermetically sealed by methods employing, but not limited to, compressive or reactive glass-to-metal sealing techniques, ceramic-to-metal sealing techniques (e.g. employing materials such as alumina, gold, platinum, ruby, sapphire, aluminum nitride (AlN), zirconia ($ZrO_2$), silicon carbide (SiC), or silicon nitride ($Si_3N_4$)), and may further employ any various types of bonding methods, including active brazing, non-active brazing, or diffusion bonding, and may also further utilize anodic bonding for bonding silicon pressure diaphragms, for example, to a metal structure, or to housing 101. Other bonding and hermeticity techniques including adhesives, including medical grade epoxies, may also be utilized for producing mechanical integrity and long-term sealing of housing 101. Further, referring to FIG. 1B, inlet pressure port, 104, may also optionally allow inlet CSF from catheter 102 to pass-through the transponder housing, 101, to an integrated exit port, 110, so as to easily allow integration with a CSF shunt, such as through tubing 111 while also sensing the inlet fluid's pressure.

Figure 1B:
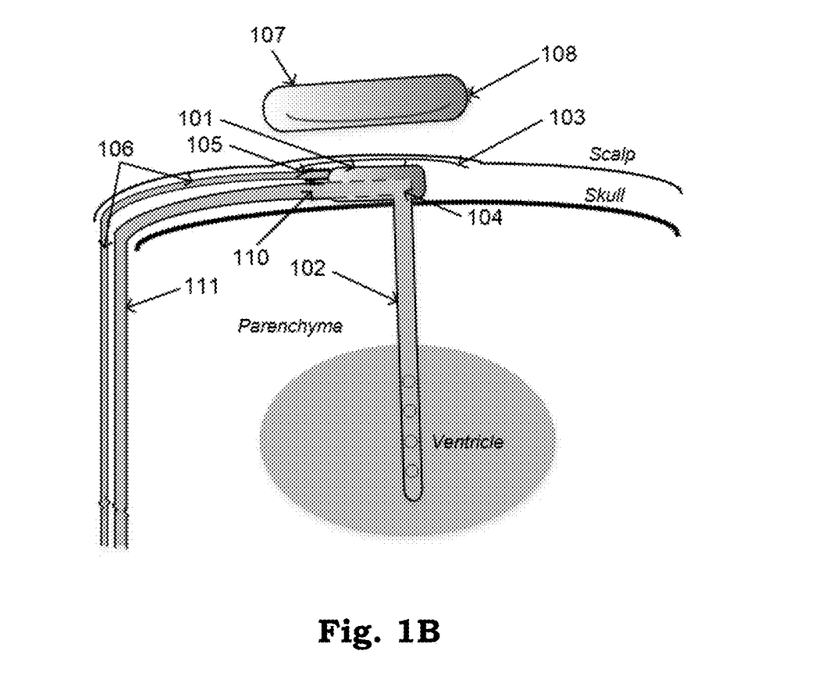
FIG. 1B is a schematic of an example embodiment of the bio-pressure sensor system showing subcutaneous implantation of the bio-pressure sensor unit, or transponder, containing multiple sensors and a CSF flow path through the transponder.

However, similar shunt integration may also be accomplished through the use of a fluidic tee connector and lumen whereby the transponder element in FIG. 1A may be connected so as to be in fluid communication with a shunt's existing ventricular catheter and shunt system, although such an integration may not offer optimum fluid dynamics as in the case of the embodiment illustrated in FIG. 1B. FIG. 1B is another example embodiment of the bio-pressure sensor system also showing subcutaneous implantation of the bio-pressure sensor unit, or transponder, containing multiple sensors, but which contains a CSF flow path through the transponder, of which CSF pressure is measured, and in which the transponder also comprises a reference fluid column for long term assessment of CSF pressure along with an ex-vivo telemetric processing unit.

Figure 1C:
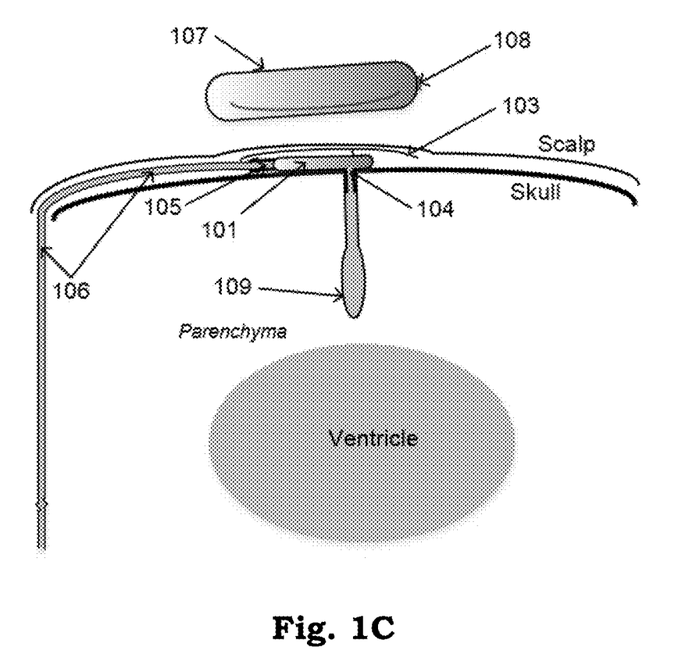
FIG. 1C is a schematic of an example embodiment of the bio-pressure sensor system showing subcutaneous implantation of the bio-pressure sensor unit with an intracranial bladder transducer and a reference fluid column.

FIG. 1C is a schematic of an example embodiment of the bio-pressure sensor system also showing subcutaneous implantation of the bio-pressure sensor unit, or transponder, containing multiple sensors, but with an intracranial bladder transducer and also a reference fluid column for long term assessment of CSF pressure along with an ex-vivo telemetric processing unit.

As shown in FIG. 1C, inlet pressure port may alternatively be stimulated by an intracranial pressure bladder, 109, which transduces ICP via a flexible membrane to a fluid contained within 109, in which the bladder's material may be impermeable to fluids over long periods of time, relative to a pressure measurement, or of a semi-impermeable type flexible material, whereby pores less than 5 μm may exist, for example. Furthermore, referring to the illustration in FIG. 1C, nothing is to prevent intracranial pressure bladder, 109, from being of such length so as to extend into the brain's ventricle for reasons of improving ICP measurement which may be desirable for a more accurate ICP assessment.

Reference pressure inlet port 105 is connected to a fluid chamber, such as a catheter, or bladder, or fluid column, 106, for atmospheric pressure sensing. The pressure presented to inlet port 105 may also be a function of position, whereby a predetermined and known fluid pressure is exerted, for example, when perpendicular to a gravitational field and then another predetermined and known pressure exerted when parallel to a gravitational field for the overall purpose of providing a variable reference pressure to the bio-pressure sensor unit for calibration purposes. The variable reference pressure may be compared to a known or expected pressure difference based on, for example, the geometry of the fluid chamber. Additionally, the reference pressure may be compared to a known environmental pressure.

The reference pressure port 105 may optionally be stimulated by a different type of controllable calibrating pressure, such as an electromagnetic piston, solenoid, or other volume modulating means, which may be actuated ex-vivo. The reference port 105 may optionally further utilize atmospheric pressure changes, known by an external calibrating apparatus and/or method, in order to utilize a changing pressure, such as that experienced by elevation changes, weather patterns, or facility conditions, which may be exploited for calibration.

Telemetry antenna 103 may optionally be located external to housing 101, but yet connected to the sensor unit, 101, such as through ceramic or glass insulating seals, and may be of the inductive, optical, or other electromagnetic type of antenna or coupling means for external powering and communications. Transceiver unit, 107, located ex-vivo, is used to telemetrically couple to implanted bio-pressure sensor transponder unit, 101, and to also accurately measure atmospheric pressure through pressure sensor 108, which may be calibrated with metrics traceable to a known and accepted standard, such as that provided by the National Institute of Standards and Technology, for example.

Figure 2:
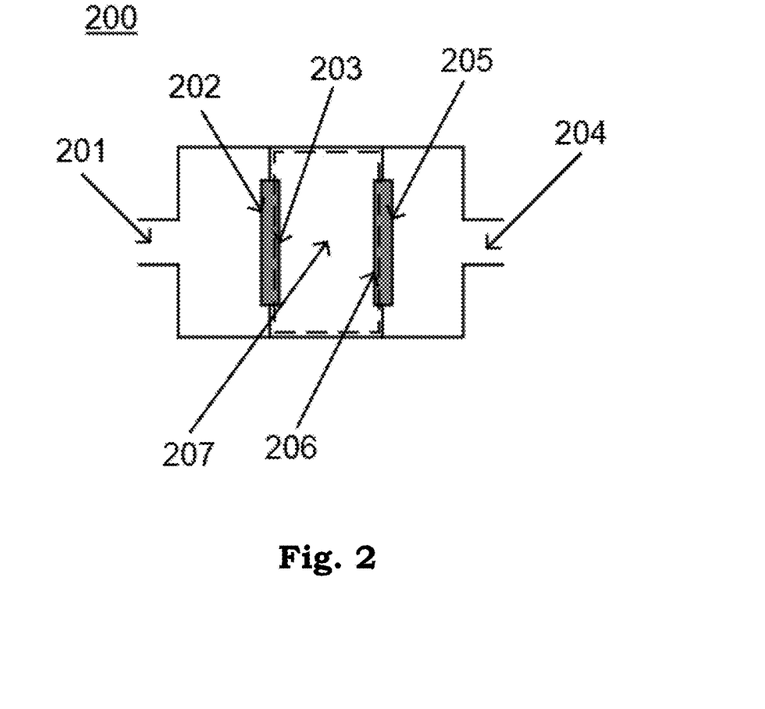
FIG. 2 is a schematic illustrating an example dual pressure sensor unit with an absolute pressure reference.

With reference to FIG. 2, there is illustrated and described a dual pressure sensor providing an overall differential pressure transducer, generally indicated by 200, with an absolute pressure reference contained within volume 207 (shown approximately by the dashed line). A first pressure port, 201, may accommodate a reference fluid such as that described by 105, for example, whereby sensor face 202 gauges such pressure, and may be of the piezo-resistive, piezo-electric, capacitive, or optical type, and is countered by the reference pressure contained within 207, which may be any pressure from vacuum or greater, thereby providing a pressure signal that is indicative of the pressure difference from that produced by inlet 201 and reference 207.

Likewise, second pressure port, 204, may accommodate CSF described by 104, for example, whereby sensor face 205 gauges such pressure, and may be of the piezo-resistive, piezo-electric, capacitive, or optical type, and is countered by the reference pressure contained within 207, which, as before, may be any pressure from vacuum or greater, thereby providing a pressure signal that is indicative of the pressure difference from that produced by inlet 204 and reference 207. In both cases, pressure sensor faces, 203, and 206 serve to translate the reference pressure and to offset that presented by inlets 201 and 204, respectively, and therefore creates a differential pressure indication between the inlets and reference pressure chamber 207.

Sensors, 202 and 205 are substantially similar or identical in error characteristics and also in packaging structure such that error signals induced by stress or strain in one sensor is common to the other such that error becomes common-mode. Nothing is to prevent however, that sensors may be placed upon or within the surfaces of 203 and 206 or any combination thereof with 202 and 205. In addition, in some embodiments sensors 202 and 205 may have different error characteristics and packaging structure relative to one another. The sensors may be fabricated from silicon or ceramic, for example, and from the same die and/or physically located nearby so as to produce similar characteristics for common-mode rejection capability and may use pressure transduction means encompassing any of the piezo-resistive, piezo-electric, capacitive, or optical types, or any other prevailing pressure transduction means.

Figure 3:
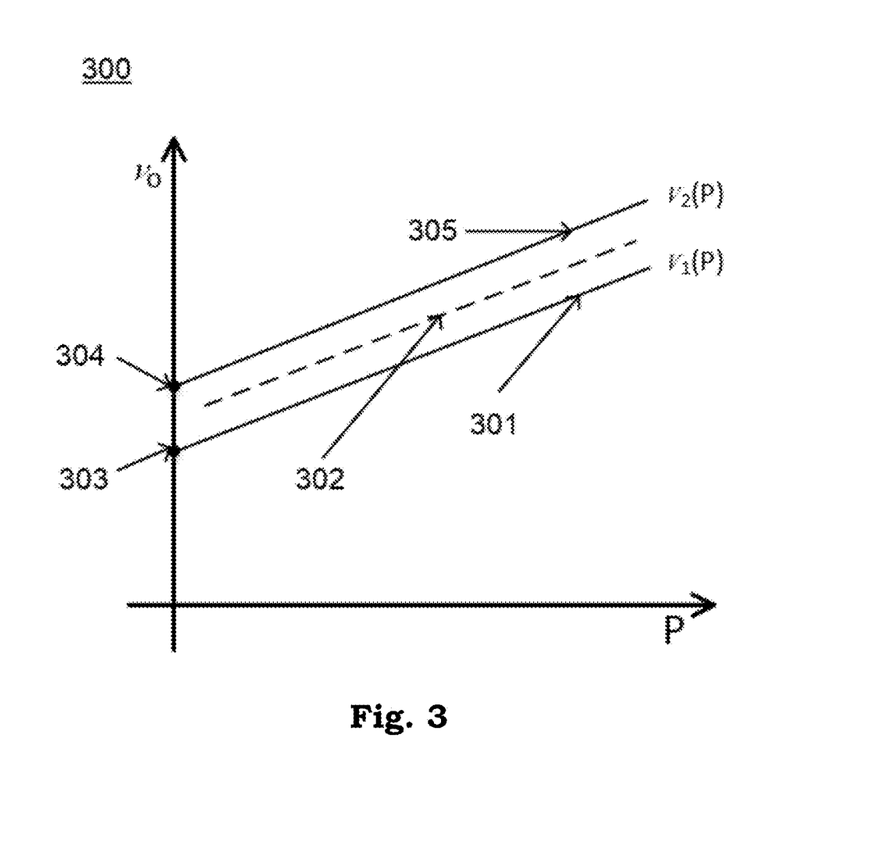
FIG. 3 is a graph illustrating example transfer functions for the two sensors embedded into the implantable bio-pressure unit.

FIG. 3 illustrates a Cartesian graph, generally denoted 300, presenting typical transfer functions for pressure sensors as a function of the input pressure, P, generating an electrical output voltage signal $v_o$. The line described by 301 represents a linear transfer function, $V_1(P)$, for a pressure sensor that may be used to measure a reference input, such as a semi-flexible fluid column aligned vertically within a patient's torso, as described by 106. Serving as a positional dependent reference, or otherwise as previously described, the transfer function for line 106 could be simplified and described by:

$$v_1(P) = (P_{atm} + P_{col}(\theta)) \cdot m_1(t) + b_1(t)$$

where $P_{atm}$ is the atmospheric pressure exerted upon the reference column, $P_{col}(\theta)$ is the positional dependent pressure induced by the reference column/element, $m_1$ is the gain of the sensor representing the slope of line 301, which is a function of time due to creep or other variables, and $b_1$ is the zero-pressure of the sensor, represented by the y-intercept, 303, of line 301, which is also a function of time due to drift caused by undesirable changes within the sensor, including but not limited to, changes in the reference pressure from volume 207 leaking over time or changes in the structure of the sensor over time.

Therefore, once the bio-pressure sensor unit is implanted, $m_1(t)$ and $b_1(t)$ become unknown characteristics. However, the reference pressure, $P_{col}(\theta)$, described by 106 is known, for example, because it presents an a priori column of fluid, or other means previously described, with well-understood density and length such that in the horizontal patient position, it exerts little to no pressure upon the sensor's 105 input, but then full negative pressure in the vertical patient position, and is overall a function of the patient's torso incline, $\theta$. In other words, for $\theta$ equal to 0°, the bio-pressure sensor's reference input presents only roughly atmospheric pressure, while for $\theta$ equal to 90°, the input receives roughly atmospheric pressure plus a negative pressure equal to the product of the fluid column's vertical volume and density and acceleration due to gravity. In any case, the function of pressure versus patient position becomes a function of the reference column's geometry and routing and may be calculated for various custom in-vivo implantations.

In all positions, however, reference column 106 is subject to and equal to atmospheric pressure since it may be constructed from a semi-pliable material compliant to barometric pressure, but yet stiff enough to resist any bodily influence upon it and furthermore, large/long enough such that any localized pressure would not adversely affect the average pressure of the column and wherein the column may be open at one end such that any localized pinching wouldn't again create noncompliant pressure to the barometric average within it. Further, such open distal end of the reference column may be located within the peritoneal cavity, without draining by virtue of its proximal sealed-end being connected to the sensor input port and since the distal open-end is within an in-vivo fluid environment, whereby it is generally expected to track barometric conditions on average, but never the less, a change in position of the fluid column also generates a change in pressure to the input of the bio-pressure sensor's reference input, 105, according to its aforementioned properties known a priori.

Line 305 of FIG. 3 illustrates a typical transfer function of a second sensor within the bio-pressure sensor unit that is a function of a second input pressure, P, which also generates an output electrical signal, $v_o$. The line described by 305 represents a linear transfer function, $V_2(P)$, for a pressure sensor that may be used to measure a bodily fluid input, such as CSF and described by:

$$v_2(P) = (P_{atm} + P_{csf}(\theta)) \cdot m_2(t) + b_2(t)$$

where $P_{atm}$ is atmospheric pressure exerted upon the fluid, $P_{csf}$ is the positional dependent fluid pressure, $m_2$ is the gain of the sensor representing the slope of line 305, which is a function of time due to creep, and $b_2$ is the zero-pressure of the sensor, represented by the y-intercept, 304, of line 305, which is also a function of time due to drift for the same reasons described of the first sensor.

Because the first and second sensors share common characteristics in packaging and sensor die, errors are shared between the two sensors as common-mode and furthermore, since they share the same absolute reference source, 207, their overall gain/slope m remains substantially the same, as illustrated by the representative interpreting line 302, and reference/offset b also remains substantially the same between the sensors such that overall $m_1(t) = m_2(t)$ and $b_1(t) = b_2(t)$. In considering calibrating the sensors for gain and offset error, since $P_{col}(\theta)$ presents an a priori known pressure delta from upright (i.e. 90°) to supine (i.e. 0°), or other such orientations, it allows the associated sensor's gain to be determined by taking two transcutaneous measurements of the first sensor, $V_1(P)$ over two positions:

$$m = \frac{v_1(90°) - v_1(0°)}{(P_{atm} + P_{col}(90°)) - (P_{atm} + \cancel{P_{col}(0°)})}$$

Note that for differing lengths (i.e. pressure magnitudes) of the fluid column, which may vary patient to patient, that both the numerator and denominator will change proportionally and not affect the slope or gain determination. It is therefore unimportant as to the length (i.e. or pressure delta capability), notwithstanding that a longer length (i.e. increased pressure delta capability) may provide an improved noise immunity, for determining the gain or slope, m, and that the length and geometry must be known a priori to ex-vivo measurements. Note also that a tube of shorter length with a higher density fluid may alternatively be used to achieve the same effect as a longer tube with a lower density fluid. In the cases described above, it has been assumed that the fluid column reference in the supine position is perfectly horizontal and presents only atmospheric pressure to its sensor without any negative pressure resulting from the fluid column. However, such simplification is for exemplification purposes only. Variations in routing of the reference's fluid column would need to be taken into account for geometry and 3-D orientation. Furthermore, the overall system may also exploit known atmospheric pressure changes, such as that due from elevation changes or weather conditions or interior conditions whether intentional or not, to also determine slope or gain and calibrate/correct the pressure sensors thereof. It follows that the y-intercept, $b_1(t) = b_2(t)$, can then be determined in the supine position where, $P_{col}(0) = 0$, according to:

$$b = v_1(P_{atm}) - (P_{atm}+) \cdot m$$

Consequently, since the ex-vivo receiving device, 107, can accurately measure barometric pressure through sensor, 108, verifiable by means of traceable calibration, $P_{atm}$ can be numerically recorded for each determination of b and compared over the course of multiple calibrations, wherein any offset/drift error over time can be tracked and corrected given the true atmospheric pressure is known, provided linearity of the sensors remains true, which is typically adequate in modern pressure sensors. Now, given the gain, m, and offset, b, have been determined and corrected for error relative to atmospheric pressure, the second sensor, $V_2(P)$, can be individually assessed (i.e. single-ended) according to:

$$v_2 = (P_{atm} + P_{csf}(\theta)) \cdot m + b$$

where $P_{csf}$ can be accurately determined for a given position. In a differential mode assessment, for $v_2 - v_1$, and for conditions whereby both the first and second sensors share atmospheric pressure as common-mode, and whereby $b_1(t)=b_2(t)$, then $$\Delta v = v_2 - v_1 = (P_{csf}(\theta) - P_{col}(\theta)) \cdot m$$

and the aforedescribed gain correction methods for m enable accurate differential mode pressure assessments.

Figure 4:
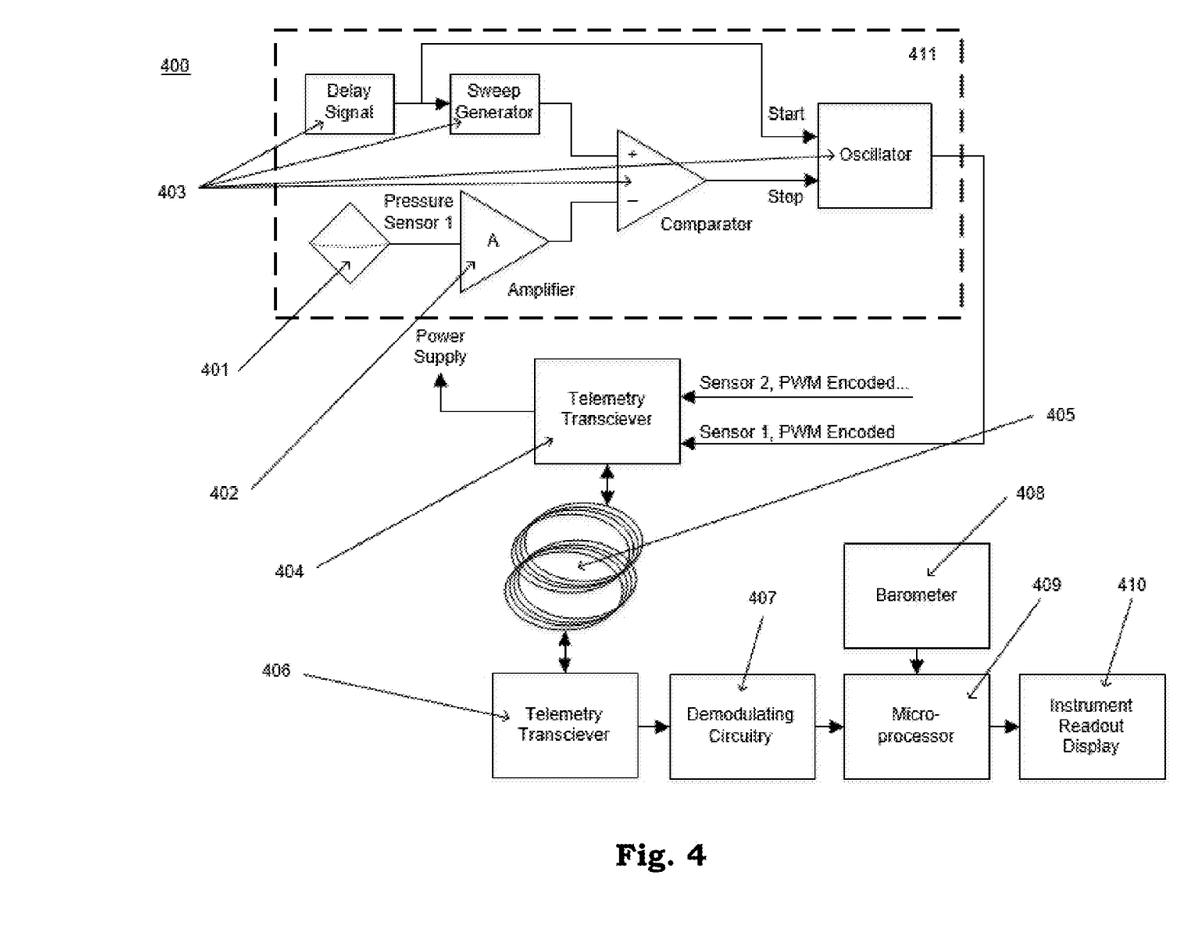

With reference to FIG. 4, there is illustrated and described electronic circuitry to support an example embodiment of an implantable bio-pressure transponder, generally referred to by 400. A first pressure sensor, 401, supplies signal proportional to pressure, which may be by means of piezo-resistive, capacitive or inductive reactance, or optical interferometry, or other transduction means, which is then conditioned by element 402, which in this embodiment is an amplifier. 403 describes an encoder for utilizing the amplified pressure sensor signal output from element 402 to modulate a communications alternating current (A.C.) carrier frequency by means of pulse width modulation. The delay element of 403 facilitates settling time of pressure sensor 401 at which point the communications oscillator is turned on and the sweep generator of 403 then begins to output a ramp signal. The ramp signal is compared to the analog pressure sensor's amplifed signal in order to generate a stop signal to the oscillator once the ramp signal equates to the analog pressure sensor signal provided through 402. Thus, the oscillator output is therefore on for the period of time that the ramp signal doesn't equate to the analog pressure sensor signal provided through amplifier 402 and then is off once the signals equate. In this way, oscillator output of 403 is proportional in time relative to the pressure incident upon 401.

Element 404 serves as a telemetry unit to facilitate power to the implanted circuit as induced from a transceiver external to the sensor and 404 also receives the encoder's oscillator circuit output to correspondingly transmit the signal across communications element 405, which may optionally be by load shift keying modulation. Telemetry transceiver 404 can further accept and encode other pressure sensors, such as a second sensor, encoded the same as generally shown in 411 by using alternative frequencies, time division multiplexing, or otherwise. Element 405 may be a low and/or high frequency inductive link, optical transceiver, or other electromagnetic coupling. Telemetry transceiver element 406 represents the ex-vivo transceiver which supplies power and transmits or receives communication to or from the bio-pressure transponder.

Element 407 represents demodulating circuitry to decode pressure sensor information from the encoding means received by 406. Element 408 is a pressure sensor, which may be traceably calibrated, to provide an accurate barometric pressure to microprocessing unit 409 for system formulations and long-term variable storage. Finally, element 410 provides the instrument's display unit for human presentation and interpretation of the patient's in-vivo pressure, which may optionally be a remote display. The example embodiment is representative of one example for implementing the invention, but does not restrict the variation for which system 411 or 404 stores long-term variable information, for example, for repeated use by calibrations, identification means, or otherwise.

Figure 5:
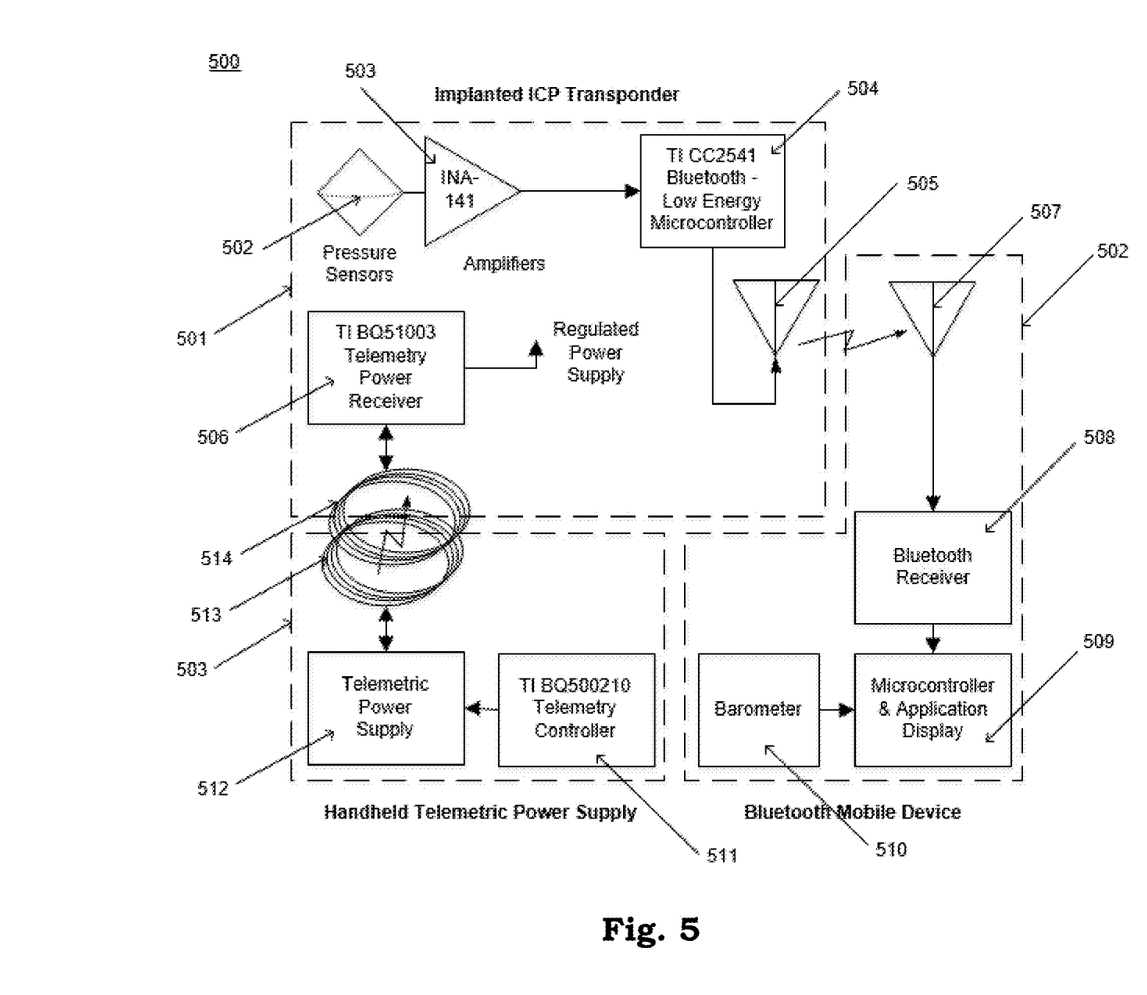

With reference to FIG. 5, there is additionally illustrated and described another example of electronic circuitry to support an example embodiment of the present general inventive concept of an implantable bio-pressure transponder, generally referred to by 500. The dotted lines of FIG. 5 are for illustration purposes only and do not necessitate or restrict the example circuitry to any particular enclosing or mechanical means of implementation. An implanted bio-pressure sensor transponder is generally referred to by 501, an ex-vivo telemetric wireless mobile processing and presentation device is generally referred to by 502, and a separate, although optionally integrated with 502, ex-vivo telemetric powering device is generally described by 503.

A plurality of pressure sensors, 502, are amplified and conditioned by amplifiers 503 which then supply's such signals to the encoding and wireless transceiver 504, which may optionally be of Bluetooth Low-Energy protocol, in communication with antenna/coupling-device 505. Antenna/coupling-device 505 telemetrically (i.e. wirelessly and percutaneously) communicates with antenna/coupling-device 507 of the ex-vivo processing/receiving device, which supplies such pressure wireless signals to a decoder 508, which may optionally be of Bluetooth Low-Energy protocol. The decoded signals are then processed by the microprocessor/microcontroller 509 for applying various algorithms, including but not limited to pressure sensor corrections/calibrations such as gain and offset correction or the application of barometric pressured measured by barometer 510, which may optionally be separate from 502. Ex-vivo telemetric powering device 503 may be comprised of electromagnetic or optical antenna/coupling-device 513 which is stimulated by the telemetric power supply 512 optionally controlled by 511. The electromagnetic or optical antenna/coupling-device 513 may then be coupled, wirelessly and percutaneously with in-vivo antenna/coupling device 514 for wirelessly receiving power by the in-vivo transponder whereby power receiver 506 rectifies and conditions such wireless energy for appropriately powering the remainder of the circuitry within 501.

I claim:

1. A bio-pressure sensor system, comprising:
a first implantable sensor to provide a reference pressure measurement;
a second implantable sensor to measure a fluid pressure associated with a bodily fluid within a human body;
a first reference element; and
a second reference element in fluid communication with the first implantable sensor, the second reference element to provide a reference pressure, the second reference element comprising a static fluid, the static fluid being different than the bodily fluid, wherein the reference pressure comprises a known first reference pressure provided at a first position and a known second reference pressure provided at a second position, the first position being defined as a reference axis being parallel with a gravitational field acting on the second reference element, and the second position being defined as the reference axis being orthogonal to the gravitational field, wherein the reference axis extends through the second reference element and orthogonal to the first implantable sensor,
wherein:
the first and second implantable sensors share the first reference element,
the second implantable sensor is not in fluid communication with the second reference element, and
the first and second implantable sensors each comprise independent output signals.

2. The bio-pressure sensor system of claim 1, wherein the second reference element is a hydrostatic device.

3. The bio-pressure sensor system of claim 1, wherein the second reference element is a tube with a first open end and a second open end in communication with the first implantable sensor.

4. The bio-pressure sensor system of claim 1, wherein the first reference element is a gas in contact with each of the first and second implantable sensors.

5. The bio-pressure sensor system of claim 1, further comprising a power unit to inductively or optically power the first and second implantable sensors.

6. The bio-pressure sensor system of claim 1, further comprising a receiver to wirelessly receive the independent output signals.

7. The bio-pressure sensor system of claim 6, wherein the receiver is at least one of a computer, a smartphone, or a mobile device.

8. The bio-pressure sensor system of claim 1, further comprising a first amplifier and a second amplifier, wherein each of the independent output signals of the first and second implantable sensors are independently provided to first and second amplifiers.

9. The bio-pressure sensor system of claim 8, further comprising an encoder and a transmitter, wherein the encoder encodes signals received from the first and second amplifiers and provides them to the transmitter, and wherein the transmitter transmits the encoded signals to the receiver.

10. The bio-pressure sensor system of claim 1, further comprising a ventricular catheter operatively coupled to the second implantable sensor, the ventricular catheter to provide fluid communication between the bodily fluid and the second implantable sensor.

11. The biopressure sensor system of claim 1, wherein the first and second implantable sensors are of substantially similar material properties and characteristics.

12. The bio-pressure sensor system of claim 1, wherein the fluid pressure associated with the bodily fluid measured by the second implantable sensor is associated with an intra-cranial pressure.

13. The bio-pressure sensor system of claim 12, further comprising a fluid-filled bladder operatively coupled to the second implantable sensor, the fluid-filled bladder to provide the intra-cranial pressure measurement.

14. A bio-pressure sensor system, comprising:
a first implantable sensor to provide a reference pressure measurement;
a second implantable sensor to measure a fluid pressure associated with a bodily fluid within a human body;
a first reference element; and
a second reference element in fluid communication with the first implantable sensor, the second reference element to provide a reference pressure, the second reference element comprising a static fluid, the static fluid being different than the bodily fluid, wherein the reference pressure comprises a known difference between a first reference pressure provided at a first position and a second reference pressure provided at a second position, the first position being defined as a reference axis being at a first angle with a gravitational field acting on the second reference element, and the second position being defined as the reference axis being at a second angle to the gravitational field, wherein the reference axis extends through the second reference element and wherein the first angle and the second angle are different,
wherein:
the first and second implantable sensors share the first reference element,
the second implantable sensor is not in fluid communication with the second reference element, and
the first and second implantable sensors each comprise independent output signals.

* * * * *